(12) United States Patent
Stokes et al.

(10) Patent No.: US 11,433,175 B2
(45) Date of Patent: *Sep. 6, 2022

(54) FOAM STRUCTURE WOUND INSERTS FOR DIRECTIONAL GRANULATION

(71) Applicant: KCI Licensing, Inc., San Antonio, TX (US)

(72) Inventors: Benjamin Stokes, Ringwood (GB); Timothy Mark Robinson, Shillingstone (GB)

(73) Assignee: KCI Licensing, Inc., San Antonio, TX (US)

( * ) Notice: Subject to any disclaimer, the term of this patent is extended or adjusted under 35 U.S.C. 154(b) by 326 days.

This patent is subject to a terminal disclaimer.

(21) Appl. No.: 16/669,672

(22) Filed: Oct. 31, 2019

(65) Prior Publication Data

US 2020/0061256 A1 Feb. 27, 2020

Related U.S. Application Data

(60) Continuation of application No. 14/867,731, filed on Sep. 28, 2015, now Pat. No. 10,493,185, which is a
(Continued)

(51) Int. Cl.
*A61F 13/00* (2006.01)
*A61M 1/00* (2006.01)
(Continued)

(52) U.S. Cl.
CPC .......... *A61M 1/90* (2021.05); *A61F 13/00017* (2013.01); *A61F 13/00068* (2013.01);
(Continued)

(58) Field of Classification Search
CPC .......... A61F 13/00017; A61F 13/00068; A61F 2013/00174; A61F 2013/00536;
(Continued)

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Chinese Second Office Action corresponding to CN 2013800054062, dated Aug. 3, 2016.
(Continued)

*Primary Examiner* — Kai H Weng

(57) ABSTRACT

A wound treatment system comprises a wound-treatment apparatus and a wound dressing coupled to the apparatus. The wound dressing includes a foam structure wound insert having pores with a greater cross-sectional area when viewed from a first direction and a smaller cross-sectional area when viewed from an orthogonal direction. Methods for making such wound inserts may include compressing foam structure material having pores with a substantially uniform cross-sectional area. Methods for treating a wound using a wound insert.

12 Claims, 7 Drawing Sheets

Related U.S. Application Data division of application No. 13/756,285, filed on Jan. 31, 2013, now Pat. No. 9,173,776.

(60) Provisional application No. 61/594,018, filed on Feb. 2, 2012.

(51) Int. Cl.
*A61L 15/42* (2006.01)
*B29C 44/56* (2006.01)

(52) U.S. Cl.
CPC ........ *A61L 15/425* (2013.01); *B29C 44/5636* (2013.01); *A61F 2013/00174* (2013.01); *A61F 2013/00536* (2013.01); *A61M 2207/00* (2013.01)

(58) Field of Classification Search
CPC ................... A61L 15/425; A61M 1/90; A61M 2207/00; B29C 44/5636
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 3,978,855 A | 9/1976 | McRae et al. |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Bustad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2006/0211781 A1 | 9/2006 | Strandburg et al. |
| 2009/0012483 A1 | 1/2009 | Blott et al. |
| 2010/0298791 A1 | 11/2010 | Jones et al. |
| 2011/0015595 A1 | 1/2011 | Robinson et al. |
| 2011/0178451 A1 | 7/2011 | Robinson et al. |
| 2011/0213320 A1 | 9/2011 | Blott et al. |
| 2011/0257572 A1 | 10/2011 | Locke et al. |

(56) References Cited

U.S. PATENT DOCUMENTS

| | | | | |
|---|---|---|---|---|
| 2012/0165715 | A1* | 6/2012 | Murphy | A61F 13/023 602/54 |
| 2014/0163491 | A1 | 6/2014 | Schuessler et al. | |
| 2015/0080788 | A1 | 3/2015 | Blott et al. | |

FOREIGN PATENT DOCUMENTS

| | | | |
|---|---|---|---|
| AU | 755496 | B2 | 12/2002 |
| CA | 2005436 | A1 | 6/1990 |
| CN | 101677876 | A | 3/2010 |
| DE | 26 40 413 | A1 | 3/1978 |
| DE | 43 06 478 | A1 | 9/1994 |
| DE | 29 504 378 | U1 | 9/1995 |
| EP | 0100148 | A1 | 2/1984 |
| EP | 0117632 | A2 | 9/1984 |
| EP | 0161865 | A2 | 11/1985 |
| EP | 0358302 | A2 | 3/1990 |
| EP | 0747420 | A1 | 12/1996 |
| EP | 1018967 | A1 | 7/2000 |
| GB | 692578 | A | 6/1953 |
| GB | 2195255 | A | 4/1988 |
| GB | 2 197 789 | A | 6/1988 |
| GB | 2 220 357 | A | 1/1990 |
| GB | 2 235 877 | A | 3/1991 |
| GB | 2 329 127 | A | 3/1999 |
| GB | 2 333 965 | A | 8/1999 |
| JP | 4129536 | B2 | 8/2008 |
| SG | 71559 | | 4/2002 |
| WO | 80/02182 | A1 | 10/1980 |
| WO | 87/04626 | A1 | 8/1987 |
| WO | 90/010424 | A1 | 9/1990 |
| WO | 93/009727 | A1 | 5/1993 |
| WO | 94/20041 | A1 | 9/1994 |
| WO | 96/05873 | A1 | 2/1996 |
| WO | 97/18007 | A1 | 5/1997 |
| WO | 99/13793 | A1 | 3/1999 |
| WO | 0102033 | A1 | 1/2001 |
| WO | 2005021622 | A2 | 3/2005 |
| WO | 2010147535 | A1 | 12/2010 |
| WO | 2011090991 | A2 | 7/2011 |

OTHER PUBLICATIONS

Japanese Notice of Rejection corresponding to JP2014-555715, dated Oct. 11, 2016.
Chinese Third Office Action corresponding to CN 2013800054062, dated Feb. 6, 2017.
European Examination Report corresponding to EP137046868, dated Apr. 6, 2017.
Australian Examination Report corresponding to Application No. 2013215067, dated Jul. 28, 2017.
Japanese Notice of Rejection corresponding to Application No. 2014555715, dated Jun. 27, 2017.
Canadian Office Action for Corresponding Application No. 2858110, dated Oct. 3, 2018.
Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.
Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT International Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GB96/02802; dated Jan. 15, 1998 & Apr. 29, 1997.
PCT Written Opinion, PCT International Application PCT/GB96/02802; dated Sep. 3, 1997.
Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al; "Vacuum Treatment in the Surgical Management of Purulent Wounds"; Vestnik Khirurgi, Sep. 1986, pp. 18-21 and 6 page English translation thereof.
Davydov, Yu. A., et al; "Vacuum Therapy in the Treatment of Purulent Lactation Mastitis"; Vestnik Khirurgi, May 14, 1986, pp. 66-70, and 9 page English translation thereof.
Yusupov. Yu.N., et al; "Active Wound Drainage", Vestnki Khirurgi, vol. 138, Issue 4, 1987, and 7 page English translation thereof.
Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "Irrigation Treatment in Split-Thickness Skin Grafting of Intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels,"

(56) References Cited

OTHER PUBLICATIONS

Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax," Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").
V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").
V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").
V.A.C.® Therapy Clinical Guidelines: A Reference Source for Clinicians; Jul. 2007.

\* cited by examiner

FOAM STRUCTURE WOUND INSERTS FOR DIRECTIONAL GRANULATION

RELATED APPLICATIONS

This application is a continuation of U.S. patent application Ser. No. 14/867,731, filed Sep. 28, 2015, which is a divisional of U.S. patent application Ser. No. 13/756,285, filed Jan. 31, 2013, which claims priority to U.S. Provisional Patent Application No. 61/594,018 filed Feb. 2, 2012, the disclosures of which are hereby incorporated by reference in its entirety.

TECHNICAL FILED

The present disclosure relates generally to healing of wounds and wound-treatment therapies. More particularly, but not by way of limitation, the present disclosure relates to fluid-instillation and negative-pressure wound therapies.

BACKGROUND INFORMATION

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue.

Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape).

SUMMARY OF ILLUSTRATIVE EMBODIMENTS

The present disclosure includes embodiments of wound inserts with pores configured to promote directional granulation during negative pressure therapy.

An exemplary embodiment of a wound insert for use with a wound dressing, wherein the wound insert comprises a foam structure having a first surface, a second surface generally parallel to the first surface, and a third surface extending between the first surface and the second surface. The wound insert further comprises a plurality of pores distributed through the foam structure in an open-cell relation forming flow channels for receiving and distributing fluid to a wound. Each pore of the plurality of pores has a first cross-sectional area parallel to the first surface and a second cross-sectional area perpendicular to the first surface wherein the first cross-sectional area of most of the pores is greater than the second cross-sectional area of the pores. The second surface is adapted to receive fluids from a source of fluid and the first surface is adapted to be disposed proximate the wound for distributing fluids to the wound. The first cross-sectional area may have an average diameter greater than or equal to about 2.0 mm. The second cross-sectional area may have an average minor axis less than or equal to about 0.5 mm.

Certain embodiments include a wound insert for use with a wound dressing, where the wound insert comprises a first surface, a second surface, a third surface extending between the first and second surfaces, and a plurality of pores distributed through the wound insert. The pores comprise an average cross-sectional area that is greater when viewed from a direction perpendicular to the first surface than the average cross-sectional area of the pores when viewed from a direction perpendicular to the third surface. In particular embodiments, the third surface is substantially perpendicular to the first and second surfaces. In specific embodiments, the wound insert is substantially rectangular in shape.

In certain embodiments, the first surface comprises a plurality of channels, and in specific embodiments the channels are approximately 1.0 mm wide. In particular embodiments, the wound insert is configured to be inserted into a wound such that the first surface is proximal to a lower portion of the wound that is distal from an epidermis. In particular embodiments, the foam structure comprises a hydrophilic foam structure.

Certain embodiments comprise a wound insert for use with a wound dressing, where the wound insert comprises a first surface and a plurality of pores, where a majority of the pores of the wound insert comprise a maximum cross-sectional area that is greater when viewed from a direction perpendicular to the first surface than when viewed from a direction parallel to the first surface. In particular embodiments, substantially all of the pores of the wound insert comprise a cross-sectional area that is greater when viewed from a direction perpendicular to the first surface than when viewed from a direction parallel to the first surface.

In particular embodiments, a majority of the pores of the wound insert comprise a substantially circular cross-section when viewed from a direction perpendicular to the first surface and a substantially oval cross-section when viewed from a direction parallel to the first surface. In certain embodiments, the majority of the pores of the wound insert comprise a substantially circular cross-section with a diameter greater than approximately 1.0 mm when viewed from a direction perpendicular to the first surface and a substantially oval cross-section with a minor axis less than approximately 0.5 mm when viewed from a direction parallel to the first surface.

Particular embodiments include a wound-treatment method comprising: positioning a wound insert on a wound of a patient, where the wound insert comprises a first surface having a plurality of pores with a first average cross-sectional area, and a second surface having a plurality of pores with a second average cross-sectional area that is less than the first average cross-sectional area; orienting the wound insert such that the first surface is proximal a bottom surface of the wound; and coupling a drape to skin adjacent the wound such that the drape covers the wound insert to form a space between the drape and the wound.

Specific embodiments also include applying negative pressure to the wound through the wound dressing. In certain embodiments, applying negative pressure comprises activating a vacuum source that is coupled to the wound dressing. Particular embodiments also include delivering a fluid to the wound through the wound dressing. In certain embodiments, delivering a fluid comprises activating a fluid source that is coupled to the wound dressing.

Particular embodiments also include a method of making a wound insert, comprising: applying a compressive force to foam structure comprising a plurality of pores, where the compressive force is applied in a first direction against a first surface; creating a reduced pore size on a second surface of the foam structure, where the second surface is substantially parallel to the first direction; and removing the compressive force from the foam structure, where the reduced pore size on the second surface of the foam structure is maintained after the compressive force is removed.

In specific embodiments, the first surface comprises a pore size greater than the reduced pore size on the second surface after the compressive force is removed. In particular embodiments, the compressive force compresses the foam structure at a ratio greater than or equal to approximately 5:1. In certain embodiments, the compressive force is applied with a heated plate. In particular embodiments, the heated plate forms a film-like structure on the first surface of the foam structure and further comprising removing the film-like structure from the first surface of the foam structure.

Details associated with the exemplary embodiments described above and any other exemplary embodiments are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

DESCRIPTION OF ILLUSTRATIVE EMBODIMENTS

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises a wound insert and a drape, the wound dressing includes the specified elements but is not limited to having only those elements. For example, such a wound dressing could also include a connection pad configured to be coupled to a wound-treatment apparatus.

Further, a device or structure that is configured in a certain way is configured in at least that way, but it can also be configured in other ways than those specifically described.

Figure 1:
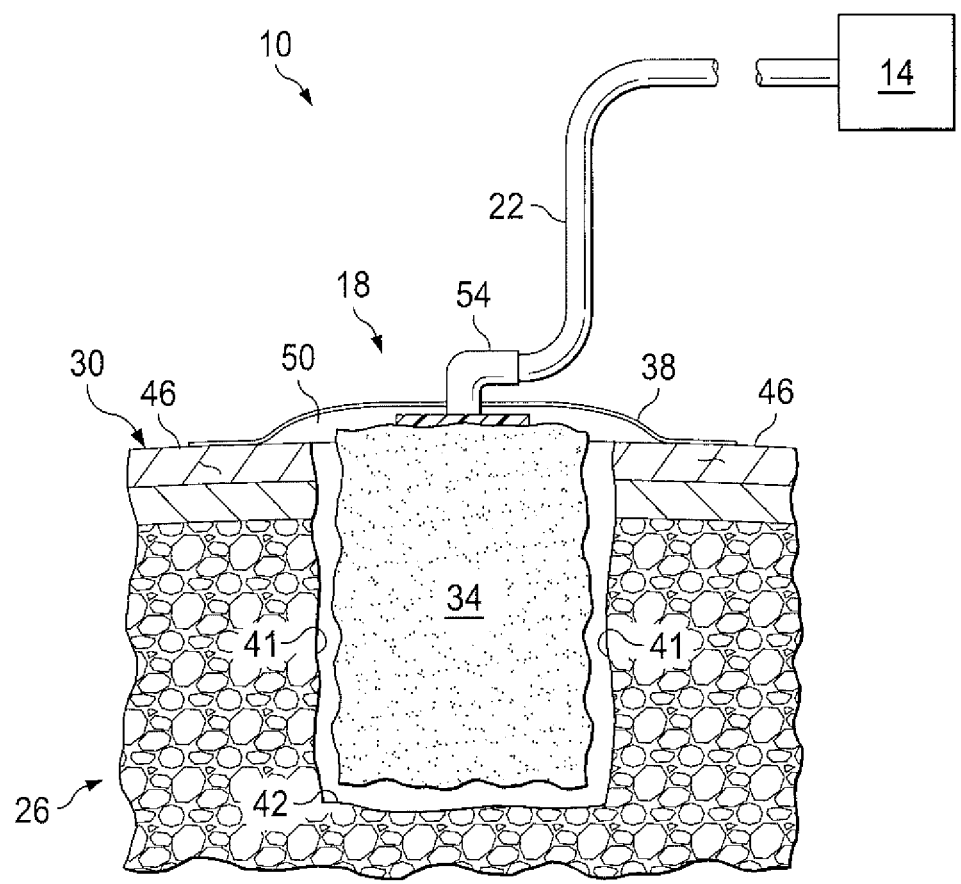
FIG. 1 depicts a side view of one embodiment of the present wound dressings having one of the present wound inserts and coupled to a wound site and to a wound treatment apparatus.

Referring now to the drawings, and more particularly to FIG. 1, shown therein is an exemplary embodiment of a wound treatment system 10. In the embodiment shown, system 10 comprises a wound-treatment apparatus 14, and a wound dressing 18 coupled to apparatus 14 by a conduit 22. As shown, dressing 18 is configured to be coupled to (and is shown coupled to) a wound 26 of a patient's epidermis 30. In this embodiment, wound 26 comprises a bottom wound surface 42 and side wound surfaces 41. In the embodiment shown, dressing 18 comprises a wound insert 34 and a drape 38. As shown, wound insert 34 is configured to be positioned (and is shown positioned) on wound 26 (e.g., on or adjacent to bottom wound surface 42), and/or drape 38 is configured to be coupled to (and is shown coupled to) skin 46 of the patient adjacent to wound 26 such that drape 38 covers wound insert 34 and wound 26, and forms a space 50 between drape 38 and wound 26 (e.g., wound surface 42).

Apparatus 14 can comprise, for example, a vacuum source configured to be actuated for applying negative pressure (e.g., via conduit 22) to wound dressing 18, a fluid source configured to be actuated for delivering (e.g., via conduit 22) a fluid (e.g., an installation fluid such as a medicinal fluid, antibacterial fluid, irrigation fluid, and or the like) to wound dressing 18. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A., and/or its subsidiary and related companies (collectively, "KCI").

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, a first lumen for the application of negative pressure and/or fluid delivery, and at least one additional lumen for coupling to pressure sensor(s) to sense pressure or negative pressure between drape 38 and surface 42. In some embodiments, conduit 22 can comprise multiple lumens (e.g., as in a single conduit with a central lumen for application of negative pressure and/or fluid delivery, and one or more peripheral lumens disposed adjacent or around the central lumen such that the peripheral lumens can be coupled to a pressure sensor to sense a pressure or negative pressure between drape 38 and surface 42 (e.g. in space 50). The lumens may be arranged with a central lumen and other lumens disposed radially around the central lumen, or in other suitable arrangements. The lumens may also be provided in separate conduits. In the embodiment shown, system 10 further comprises a wound dressing connection pad 54 configured to be coupled (and is shown coupled) to conduit 22. One example of a suitable connection pad 54 is the "V.A.C. T.R.A.C.® Pad," commercially available from KCI. One example of a suitable drape 38 includes the "V.A.C.® Drape" commercially available from KCI.

Figure 2:
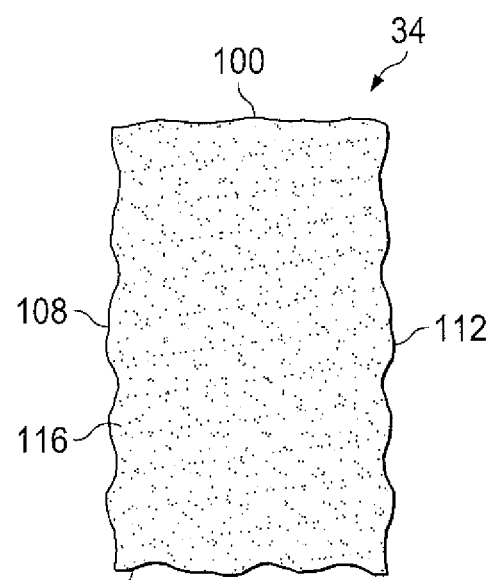
FIG. 2 depicts an enlarged side view of the wound insert of FIG. 1 disposed at the wound site.

Referring now to FIG. 2, a side view of a wound insert 34 is shown. Wound insert 34 has an upper side 100, a lower side 104, lateral sides 108, 112 and interior volume 116. Although only one side is shown of wound insert 34, it will be understood by those of ordinary skill in the art that wound insert 34 includes a three-dimensional rectangular volume having a depth extending perpendicular to the side shown. In other embodiments, wound insert 34 can have any suitable shape, such as, for example, a round cylindrical shape, a fanciful shape, or may be trimmed to fit an irregular shape of a wound (e.g., 26 and/or wound surface 42). Wound insert 34 can comprise foam structure, such as, for example, open-celled foam structure (which may also be reticulated).

Figure 3:
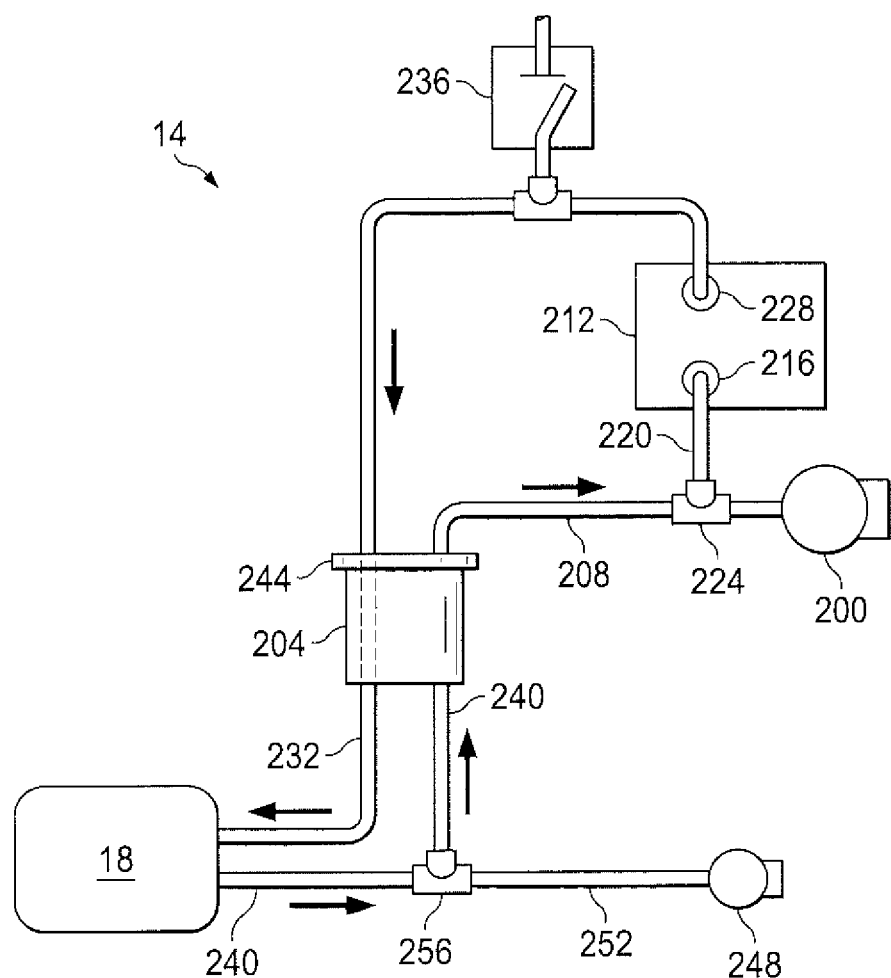
FIG. 3 depicts a schematic block diagram of one embodiment of a wound treatment apparatus that can comprise and/or be coupled to and/or be used with the present wound dressings and/or wound inserts.

Embodiments of the present wound treatment methods may be better understood with reference to FIG. 3, which depicts a schematic block diagram of one embodiment of system 10. In the embodiment shown, wound dressing 18 is coupled to apparatus 14, and apparatus 14 comprises a vacuum source 200 (e.g., a vacuum pump and/or the like) coupled to a canister 204 (e.g., configured to receive bodily fluids and or the like from wound dressing 18) by way of a conduit 208. In the embodiment shown, apparatus 14 further comprises: a pressure sensor 212 having a first pressure transducer 216 coupled to conduit 208 by way of conduit 220 and/or tee-fitting 224, and a second pressure transducer 228 coupled to canister 204 and/or wound dressing 18 by way of conduit 232. Pressure sensor 212 is configured to sense the negative pressure in wound dressing 18, and/or any of the various lumens (e.g., within conduits) coupled to wound dressing 18, pressure sensor 212, and/or vacuum source 200.

In the embodiment shown, apparatus 14 further comprises a pressure release valve 236 coupled to conduit 232. Further, in the embodiment shown, canister 204 and vacuum source 200 are coupled to wound dressing 18 by way of conduit 240; and/or canister 204 can comprise a filter 244 at or near an outlet of canister 204 to prevent liquid or solid particles from entering conduit 208. Filter 244 can comprise, for example, a bacterial filter that is hydrophobic and/or lipophobic such that aqueous and/or oily liquids will bead on the surface of the filter. Apparatus 14 is typically configured such that, during operation, vacuum source 200 will provide sufficient airflow through a filter 244 that the pressure drop across filter 244 is not substantial (e.g., such that the pressure drop will not substantially interfere with the application of negative pressure from wound dressing 18 from vacuum source 200).

In the embodiment shown, apparatus 14 further comprises a fluid source 248 coupled to wound dressing 18 by way of a conduit 252 that is coupled to conduit 240 such as, for example, by way of a tee- or other suitable fitting 256. In some embodiments, tee fitting 256 can comprise a switch valve and/or the like such that communication can be selectively permitted between wound dressing 18 and vacuum source 200, or between wound dressing 18 and fluid source 248. In some embodiments apparatus 14 comprises only one of vacuum source 200 and fluid source 248. In embodiments of apparatus 14 that comprise only fluid source 248, canister 204 and/or pressure sensor 212 can also be omitted. In various embodiments, such as the one shown, conduit 232 and/or conduit 240 and/or conduit 252 can be combined and/or comprised in a single multi-lumen conduit, such as is described above with reference to FIG. 1. In some embodiments, fluid source 248 is coupled directly to wound dressing 18 (e.g., conduit 252 is coupled one end to wound dressing 18, such as via connection pad 54, and conduit 252 is coupled on the other end to fluid source 248; and conduit 252 is not coupled to tee fitting 256).

In various embodiments, such as the one shown in FIG. 3, apparatus 14 can be configured such that as soon as liquid in the canister reaches a level where filter 244 is occluded, a much-increased negative (or subatmospheric) pressure occurs in conduit 208 and is sensed by transducer 216. Transducer 216 can be connected to circuitry that interprets such a pressure change as a filled canister and signals this by means of a message on an LCD and/or buzzer that canister 204 requires emptying and/or replacement, and/or that automatically shuts off or disables vacuum source 200.

Apparatus 14 can also be configured to apply negative (or subatmospheric) pressure (e.g., continuously, intermittently, and/or periodically) to the wound site, and/or such that pressure relief valve 236 enables pressure at the wound site to be brought to atmospheric pressure rapidly. Thus, if apparatus 14 is programmed, for example, to relieve pressure at ten-minute intervals, at these intervals pressure relief valve 236 can open for a specified period, allow the pressure to equalize at the wound site, and then close to restore the negative pressure. It will be appreciated that when constant negative pressure is being applied to the wound site, valve 236 remains closed to prevent leakage to or from the atmosphere. In this state, it is possible to maintain negative pressure at the wound site without running and/or operating pump 200 continuously, but only from time to time or periodically, to maintain a desired level of negative pressure (i.e. a desired pressure below atmospheric pressure), which is sensed by transducer 216. This saves power and enables the appliance to operate for long periods on its battery power supply.

Figure 4:
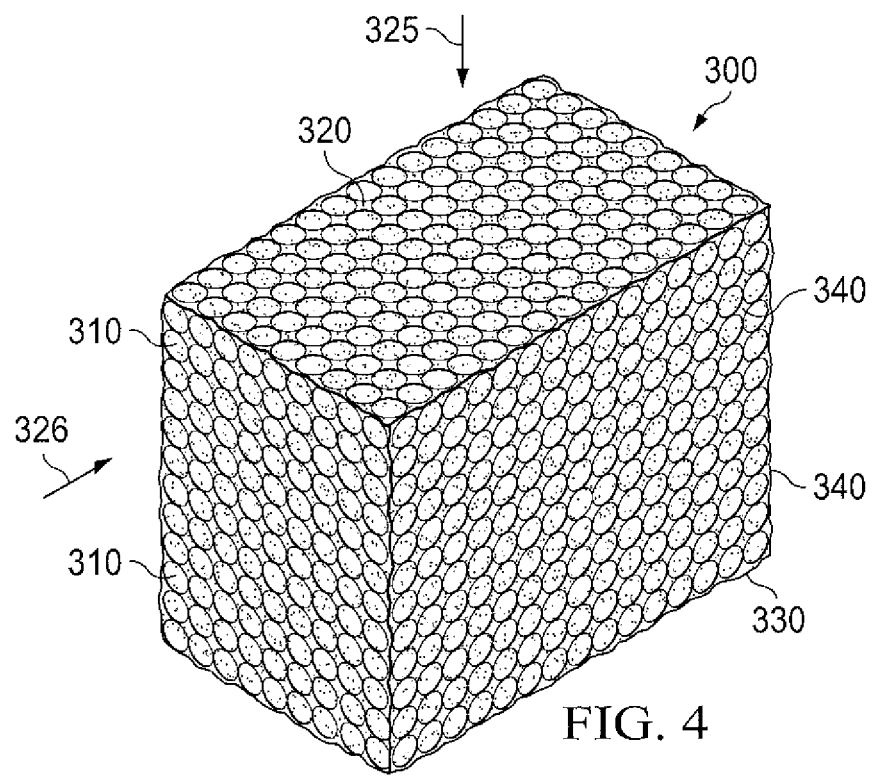
FIG. 4 depicts a perspective view of an embodiment of a foam structure component having an open-cell structure.

Referring now to FIGS. 4-9, various views are shown of several embodiments of the present wound inserts and components used to form such inserts. FIG. 4 depicts a perspective view of a foam structure component or foam structure 300 that includes a plurality of pores 310 that may be substantially spherical and uniform in size. The foam structure 300 has an open-cell structure so that a substantial number of the pores 310 are interconnected to form flow channels through which negative pressure may be applied to the wound. Foam structure 300 comprises a first surface 320 and a substantially parallel second surface 330, as well as a plurality of surfaces 340 extending between first and second surfaces 320, 330. As illustrated in this view, pores 310 comprise a cross-section that is substantially similar in size and shape, regardless of which direction foam structure 300 is viewed from. For example, if viewed in the direction indicated by arrow 325 (e.g., perpendicular to first surface 320) pores 310 comprise a cross-section that is substantially spherical and similar in size. If viewed from a direction parallel to first surface 320 (and perpendicular to arrow 325 and one of surfaces 340 as indicated by arrow 326), pores 310 also comprise a cross section that is generally equivalent in size and shape to the cross-section viewed in the direction of arrow 325.

Figure 5:
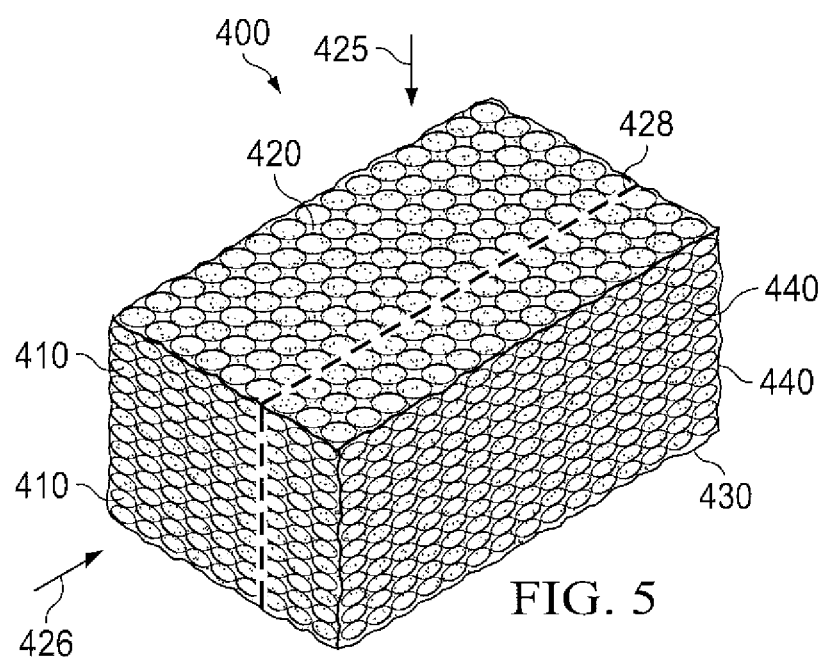
FIG. 5 depicts a perspective view of an embodiment of a compressed foam structure component having an open-cell structure.

Referring now to FIG. 5, a perspective view of foam structure 400 is shown comprising a plurality of pores 410 that are not substantially similar in size when viewed from different directions. Foam structure 400 comprises a first surface 420 and a substantially parallel second surface 430 as well as a plurality of surfaces 440 extending between first and second surfaces 420, 430. As illustrated in this view, pores 410 comprise a cross-section that is substantially circular and similar in size and shape when viewed in the direction indicated by arrow 425 (e.g., perpendicular to first surface 420). However, if viewed from a direction parallel to first surface 420 (and perpendicular to arrow 425 and one of surfaces 440 as indicated by arrow 426), pores 410 comprise a cross-section that is substantially oval rather than circular in shape (and smaller than the cross-section when viewed in the direction indicated by arrow 425). Pores 410 therefore comprise a cross-sectional area that is greater when viewed from a direction perpendicular to the first surface 420 (arrow 425) than when viewed from a direction parallel to the first surface 420 (arrow 426). To describe this in other words, the pores 410 have a first cross-sectional area parallel to the first surface 420 that on average is greater than a second cross-sectional area perpendicular to the first surface 420.

As described above, the foam structure 300 has an open-cell structure so that a substantial number of pores for 10 are interconnected to form flow channels through which fluids such as, for example, negative pressure or liquids may be applied to the wound. Consequently, when such fluids are applied to the foam structure 400, airflow through the foam structure 400 via the flow channels formed by the pores 410 is greater in the direction perpendicular to the first surface 420 (arrow 425) than in the direction parallel to the first surface 420 (arrow 426). The reduction of airflow through the flow channels in a direction parallel to the first surface 420 is partially caused as a result of the pores 410 being compressed or flattened in the direction perpendicular to the first surface 420. The reduction in airflow via flow channels having this smaller cross-section formed by a series of pores 410 in a direction parallel to the first surface 420 can inhibit granulation of the surface of a wound adjacent the third surface 440.

While pores 410 are shown in FIG. 5 to be identical in size and shape when viewed from a particular direction, it is understood that the pores 410 may very in size and shape and not be uniform throughout the foam structure 400 as will be illustrated in more detail below. However, for purposes of illustration, the pores 410 in this exemplary embodiment comprise a substantially circular cross-section with a diameter greater than or equal to approximately 1.0 mm when viewed from a direction perpendicular to first surface 420 (arrow 425). In other exemplary embodiments, pores 410 may comprise a substantially circular cross-section with a diameter greater than or equal to approximately 2.0 mm when viewed from a direction perpendicular (arrow 425) to first surface 420. In other exemplary embodiments, pores 410 may also comprise a substantially oval cross-section with a minor axis less than or equal to approximately 0.5 mm when viewed from a direction parallel to first surface 420 (arrow 426).

In particular embodiments, foam structure 400 may be formed by modifying foam structure with substantially spherical pores (including e.g., foam structure 300 illustrated in FIG. 4). For example, foam structure 300 may be heat compressed or felted in the depth direction of arrow 325 to create a reduced pore size on foam structure surfaces substantially parallel to the direction of compression. In certain exemplary embodiments, foam structure 300 may be compressed at a ratio greater than or equal to approximately 5:1 (e.g., overall the dimension of foam structure 300 parallel to direction 325 is reduced by a factor of 5). In certain exemplary embodiments, foam structure 300 may be compressed at a ratio greater than or equal to approximately 6:1, 7:1, 8:1, 9:1 or 10:1. In still other exemplary embodiments, foam structure 300 may be compressed at a ratio less than or equal to approximately 5:1. In other specific embodiments, heated plates can be used to compress foam structure 400 to create the pore geometry illustrated in FIG. 5. In such embodiments, the outer layer of pores that contacts the heated plates may form a film-like structure with closed pores which can be removed prior to use at the wound site.

As shown in FIGS. 4 and 5, the reduction in size between pores 310 and 410 can be achieved by the flattening of individual pores as suggested above, in which the pores undergo a shape change from substantially spherical shape to a more elliptical shape (e.g., substantially circular in cross-section when viewed from one direction and substantially oval in cross section when viewed from a direction perpendicular to the first direction). As indicated above, the flattening of the individual pores 410 in a direction perpendicular to the first surface 420 reduces airflow through the flow channels in a direction parallel to the first surface 420.

In exemplary embodiments, a foam structure component similar to foam structure 400 may be further separated into multiple sections to form multiple wound inserts. For example, the foam structure 400 may be sliced along dashed line 428 to form a separate wound insert such as, for example, wound insert 500 shown in the perspective view of FIG. 6A. Wound insert 500 can be suitable for use in deep, narrow wounds as discussed more fully below. Wound insert 500 comprises a first surface 520 and a substantially parallel second surface 530 as well as a plurality of surfaces 540 extending between first and second surfaces 520, 530. Wound insert 500 further comprises a plurality of pores 510 distributed throughout wound insert 500. as illustrated in this view, pores 510 comprise a cross-section that is substantially circular and similar in size and shape when viewed in the direction indicated by arrow 525 (e.g., perpendicular to first surface 520). However, if viewed from a direction parallel to first surface 520 (and perpendicular to arrow 525 and one of the services 540 as indicated by arrow 526), pores 510 comprise a cross-section that is substantially oval rather than circular in shape (and smaller than the cross-section when viewed in the direction indicated by arrow 525). Thus, pores 510 comprise a cross-sectional area that is greater when viewed from a direction perpendicular to the first surface 520 (arrow 525) than when viewed from a direction parallel to the first surface 520 (arrow 526).

Figure 6A:
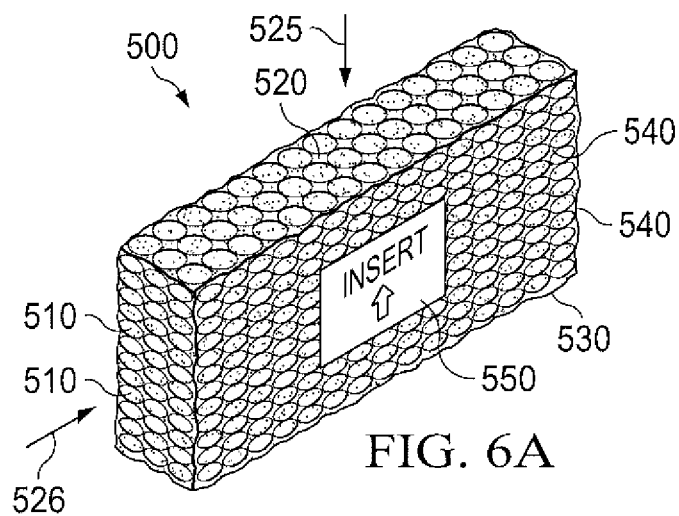
FIG. 6A depicts a perspective view of a first exemplary embodiment of a wound insert severed from the foam structure component of FIG. 5.
Figure 6B:
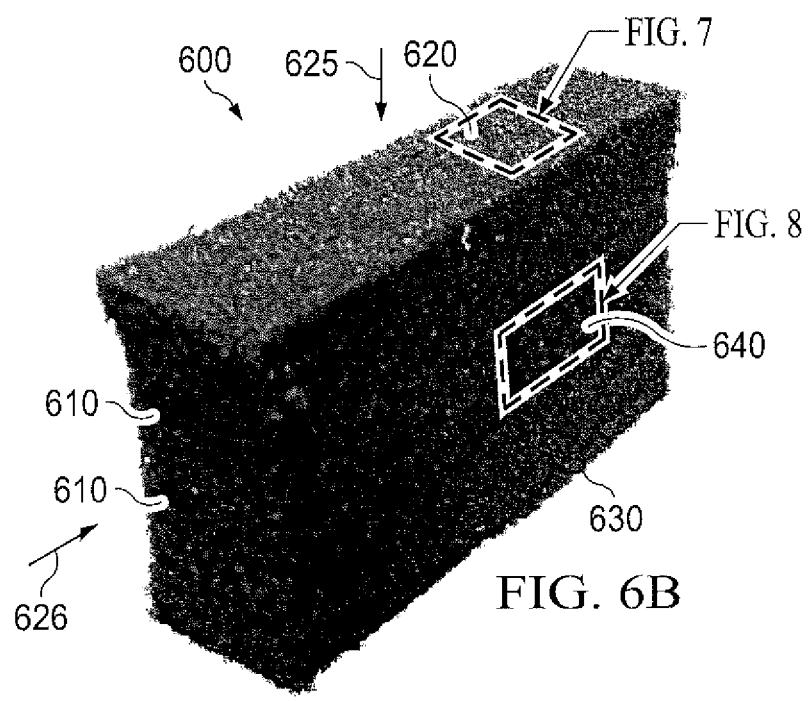
FIG. 6B depicts a photograph that is a perspective view of a second exemplary embodiment of a wound insert similar to the wound insert of FIG. 6A.

FIG. 6B depicts a photograph that is a perspective view of a second exemplary embodiment of a wound insert similar to the wound insert of FIG. 6A. The wound insert 500 is a schematic view showing that the pores 510 have substantially uniform cross-section, i.e., circular when viewed in the perpendicular direction and oval when viewed in the parallel direction. However, the cells 610 of the wound insert 600 are not uniform in shape when viewing the first surface 620 from a direction perpendicular to the first surface 620 (See FIG. 7) as illustrated by arrow 625 and when viewing the surface 640 from a direction parallel to the first surface 620 (See FIG. 8) as illustrated by arrow 626.

Figure 7:
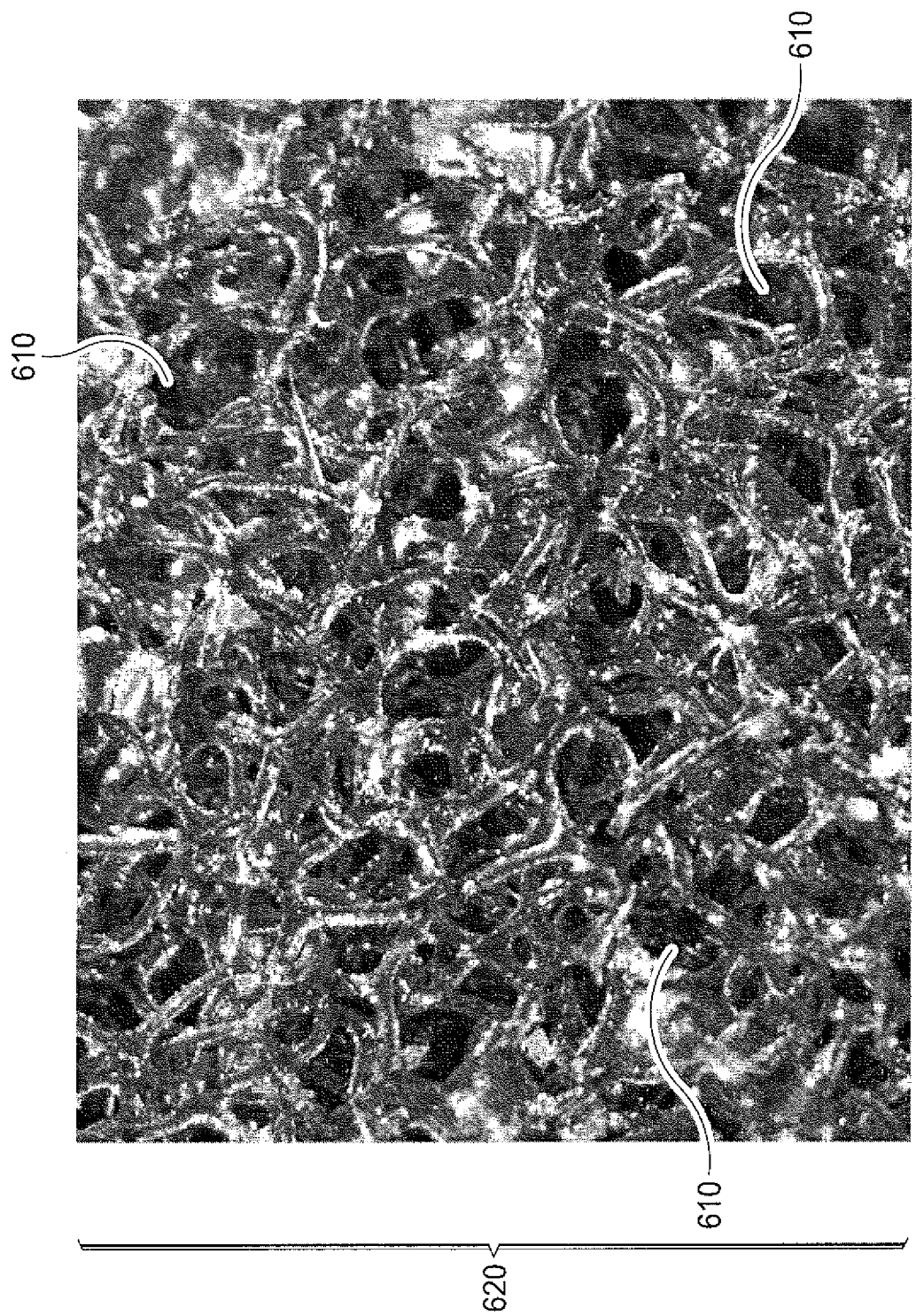
FIG. 7 depicts a photograph of a first surface of the wound insert of FIG. 6B.
Figure 8:
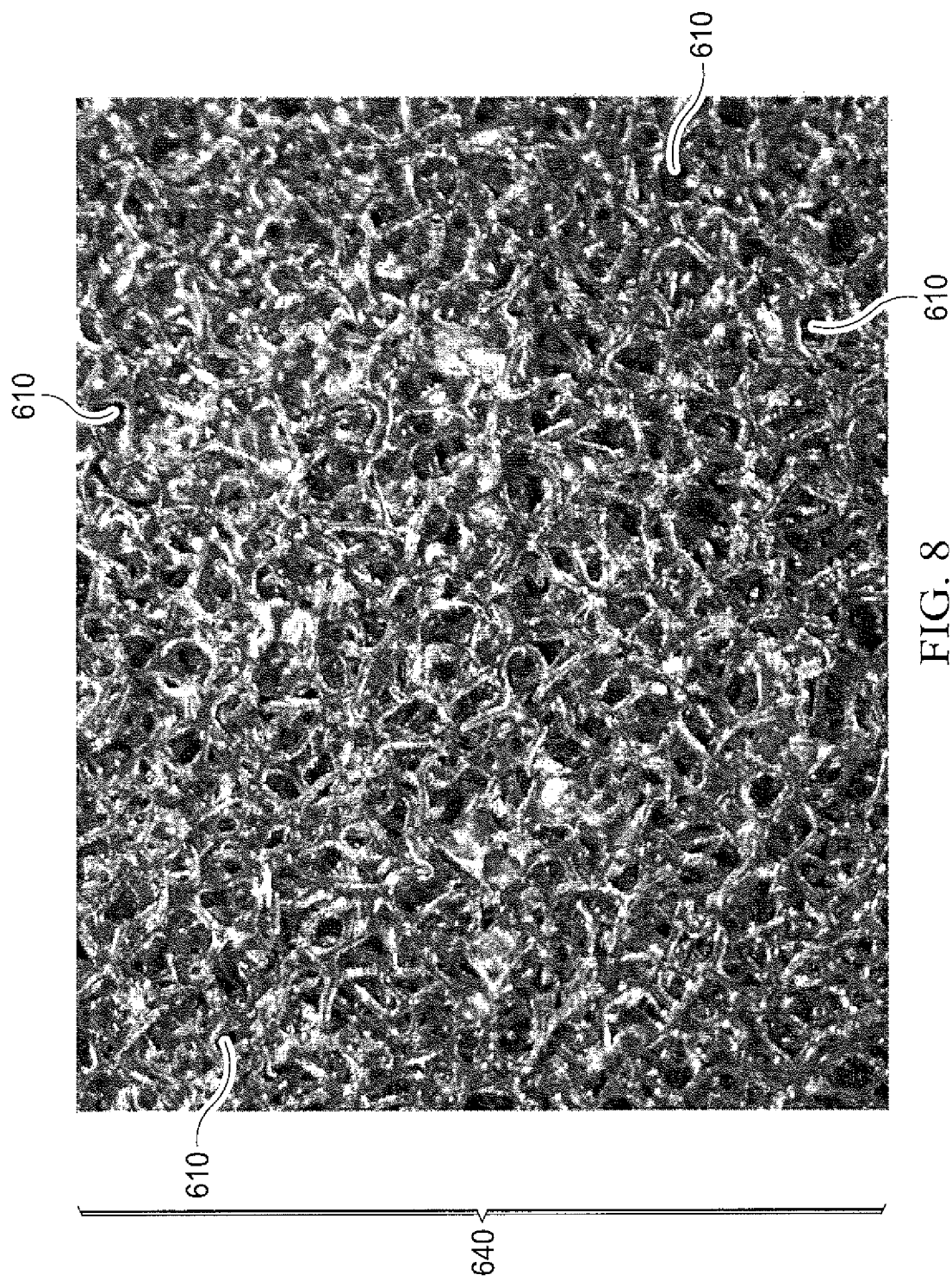
FIG. 8 depicts a photograph of a second surface of the wound insert of FIG. 6B.

FIG. 7 provides a more detailed view of pores 610 when viewed perpendicular to first surface 620, while FIG. 8 provides a more detailed view of pores 610 when viewed parallel to first surface 620 (and perpendicular to a surface 640). As illustrated in FIGS. 7 and 8, pores 610 comprise a cross-sectional area that is greater when viewed from a direction perpendicular to first surface 620 (e.g., in FIG. 7) than when viewed from a direction parallel to first surface 620 (e.g., in FIG. 8). Thus, pores 610 comprise a cross-sectional area that is greater when viewed from a direction perpendicular to the first surface 620 (arrow 525) than when viewed from a direction parallel to the first surface 620 (arrow 526) where they appear to be flattened as illustrated in FIG. 8 as a result of the original foam structure component such as, for example, foam structure 400 being compressed to form the wound insert 600.

During use, wound inserts 500, 600 can promote directional granulation in a wound surface as described above. For example, when negative pressure is applied to the foam structure 500, 600, airflow through the foam structure via the flow channels formed by the pores 510, 610 is greater in the direction perpendicular to the first surface 520, 620 that in the direction parallel to the first surface. More specifically, wound inserts 500, 600 can promote granulation in a wound surface proximal to first surfaces 520, 620 which can be located near the bottom of a wound (e.g. similar to a wound surface 42 in FIG. 1). The larger cross-sectional area of the pores 510, 610 at first surfaces 520, 620 can promote granulation, while the smaller cross-sectional area of the pores 510, 610 on the side surfaces 540, 640 between first surfaces 520, 620 and second surfaces 530, 630 can inhibit granulation (e.g. on side wound surfaces 41 in FIG. 1). Minimizing granulation between the side surfaces 540, 640 and the side surfaces of an incision, for example, can facilitate removal of wound inserts 500, 600 from the incision so that the removal of wound inserts 500, 600 is less painful for a patient.

Particularly in deep, narrow wounds, granulation of side walls in the wound can lead to premature closing of the wound and the formation of undesirable voids within the wound. In addition, side wall granulation in such wounds can make removal of the wound insert difficult and painful for the patient. In certain instances, portions of a wound insert or dressing unlike the embodiments described above can be torn from the main body of the wound insert during removal as a result of too much granulation by the sidewalls of the wound. Consequently, those granulized portions might accidentally be left in the wound causing infection and other problems.

A wound insert configured similar to wound inserts 500, 600 can address these issues by promoting wound healing at the bottom of the wound while inhibiting wound healing at the sides of the wound. In certain embodiments, wound inserts 500, 600 may comprise indicia 550 providing instructions on the proper direction of insertion into a wound as shown in FIG. 6A. Indicia 550 may comprise an arrow and/or surface labels as shown to provide a user instructions on the proper orientation of the wound insert so that first surfaces 520, 620 are proximal to the lower portion of the wound distal from the epidermis.

Figure 9:
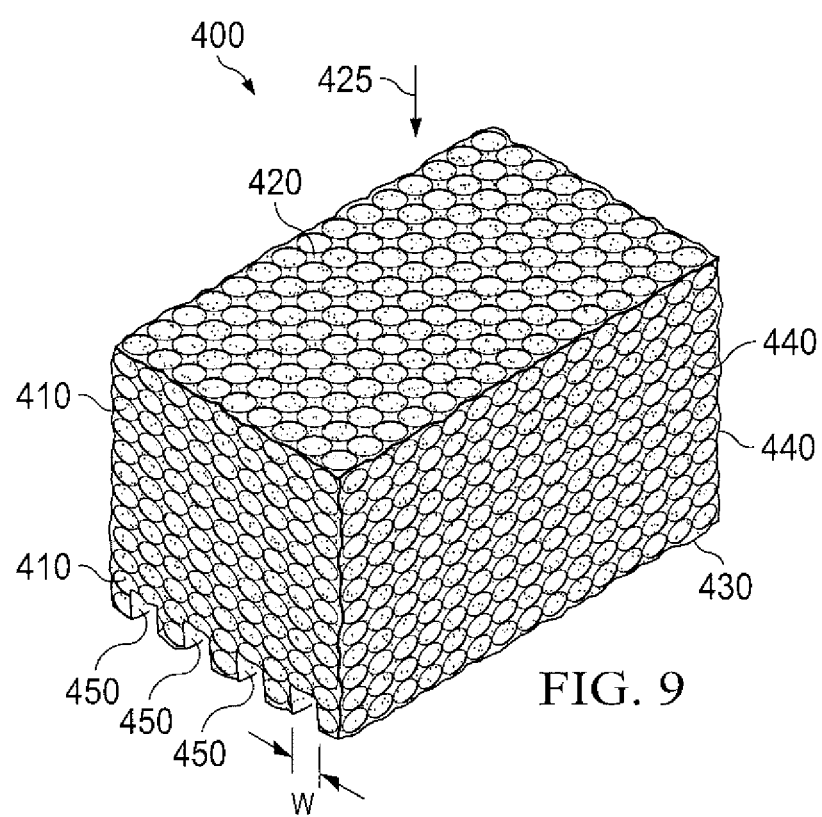
FIG. 9 depicts a perspective view of a second exemplary embodiment of a wound insert.

In exemplary embodiments, a user may cut or trim wound inserts 500, 600 to a desired size or shape and retain the geometric properties that promote directional granulation. In other exemplary embodiments, a wound insert may have other shapes or features that promote directional granulation. Referring to FIG. 9, for example, foam structure 400 is generally equivalent to that illustrated in FIG. 5 (and like reference numbers are provided in FIG. 9 for reference to features described in the embodiment of FIG. 5). The embodiment of FIG. 9, however, also includes channels 450 in surface 430 to enhance granulation. In specific embodiments, channels 450 may comprise a width W equivalent to approximately 1 mm. Channels 450 may be created during manufacturing by forming foam structure 400 in a mold that comprises recessed channels or raised portions (including for example, rods or pins). In certain embodiments, foam structure 400 may be perforated prior to the compression or felting process in order to promote the formation of channels 450.

Exemplary embodiments of manufacturing wound inserts according to the present disclosure can also comprise cooling the foam structure (e.g., after heating the foam structure) such that the compressed portion of the foam structure remains substantially compressed at room temperature (e.g., at a temperature of 72 degrees Fahrenheit) in the absence of a compressive force. In other embodiments, cooling the foam structure includes cooling a coating that has been applied to the foam structure such that the compressed portion remains substantially compressed in the absence of a compressive force at a temperature or temperature range equal to, less than, greater than, or between any of 10, 20, 30, 40, 50, 60, 70, 80, 90, 100, 110, 120, 130, 140, and/or 150 degrees Fahrenheit.

The various illustrative embodiments of devices, systems, and methods described herein are not intended to be limited to the particular embodiments disclosed. Rather, they include any modifications and alternative features that may fall within the scope of the claims.

It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate, and may be accomplished by embodiments other than those described herein that are covered by the method claims.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this invention.

The invention claimed is:

1. A system for treating a wound, the system comprising:
    a vacuum source;
    a single-layer foam structure configured to be fluidly coupled to the vacuum source, the foam structure comprising:
        a first surface having a first plurality of pores with a first average cross-sectional area; and
        a second surface having a second plurality of pores with a second average cross-sectional area, wherein the first average cross-sectional area is perpendicular to the second average cross-sectional area; and a drape configured to cover the foam structure and the wound;

wherein the first plurality of pores is configured to allow greater airflow than the second plurality of pores if negative pressure from the vacuum source is applied to the foam structure.

2. The system of claim 1, wherein the reduction of airflow through the second plurality of pores is configured to inhibit granulation of the wound adjacent to the second surface.

3. The system of claim 1, wherein the second average cross-sectional area is less than the first average cross-sectional area.

4. The system of claim 1, wherein the first average cross-sectional area comprises a diameter no less than 2 millimeters.

5. The system of claim 1, wherein the second average cross-sectional area has a minor axis less than or equal to about 0.5 millimeters.

6. The system of claim 1, further comprising indicia positioned on the second surface configured to indicate the correct orientation of the foam structure within the wound.

7. The system of claim 1, wherein the first surface is configured to be proximate to a bottom surface of the wound and the second surface is configured to be proximate to a side surface of the wound.

8. A wound insert for use with a wound dressing, the wound insert comprising:

a single-layer foam structure having a first surface and a second surface, wherein the first surface is configured to be proximate to a bottom surface of a wound and the second surface is configured to be proximate to a side surface of the wound; and a plurality of pores through the foam structure interconnected to form flow channels through which fluids may be distributed to the wound;

wherein the plurality of pores are configured to permit a greater airflow through the first surface than through the second surface if negative pressure from a vacuum source is applied to the foam structure, wherein the reduction of airflow through the second surface is configured to inhibit granulation of the wound adjacent to the second surface.

9. The wound insert of claim 8, wherein the second surface is substantially perpendicular to the first surface.

10. The wound insert of claim 8, further comprising indicia positioned on the second surface configured to indicate the correct orientation of the foam structure within the wound.

11. The wound insert of claim 8, wherein the wound insert is substantially rectangular in shape.

12. The wound insert of claim 8, wherein the first surface is a granulating surface.

* * * * *